United States Patent
Wu

[11] Patent Number: 6,161,820
[45] Date of Patent: Dec. 19, 2000

[54] CONTAINER FOR AROMATIC MATERIALS

[76] Inventor: Wen-Fu Wu, 6F, No. 440-2, Gin Pin Road, Chong-Ho City, Taipei Hsien, Taiwan, 235

[21] Appl. No.: 09/306,058

[22] Filed: May 6, 1999

[51] Int. Cl.[7] .................................................. B01F 3/04
[52] U.S. Cl. .............................. 261/104; 261/DIG. 88; 239/55; 239/57; 422/123
[58] Field of Search ................................ 261/101, 104, 261/DIG. 17, DIG. 88, DIG. 89; 239/55, 57; 422/123, 124; 446/72, 73

[56] References Cited

U.S. PATENT DOCUMENTS

| | | | |
|---|---|---|---|
| 5,407,642 | 4/1995 | Lord | 422/122 |
| 6,080,367 | 6/2000 | Lin | 422/124 |

FOREIGN PATENT DOCUMENTS

| | | | |
|---|---|---|---|
| 2430238 | 3/1980 | France | 422/124 |

Primary Examiner—David A. Simmons
Assistant Examiner—Robert A. Hopkins

[57] ABSTRACT

A container includes a housing attached to a block for receiving the aromatic material and having a number of orifices for allowing the perfume of the aromatic material to be blown out of the housing. A frame includes a track for slidably supporting the block. One or more wheels are rotatably secured to the frame and coupled to the block by cranks and links and legs. A light bulb is attached to the block, and a switch may be used to control the operation of the light bulb. The block may be attached to a support device by a clipper or the other fasteners.

11 Claims, 6 Drawing Sheets

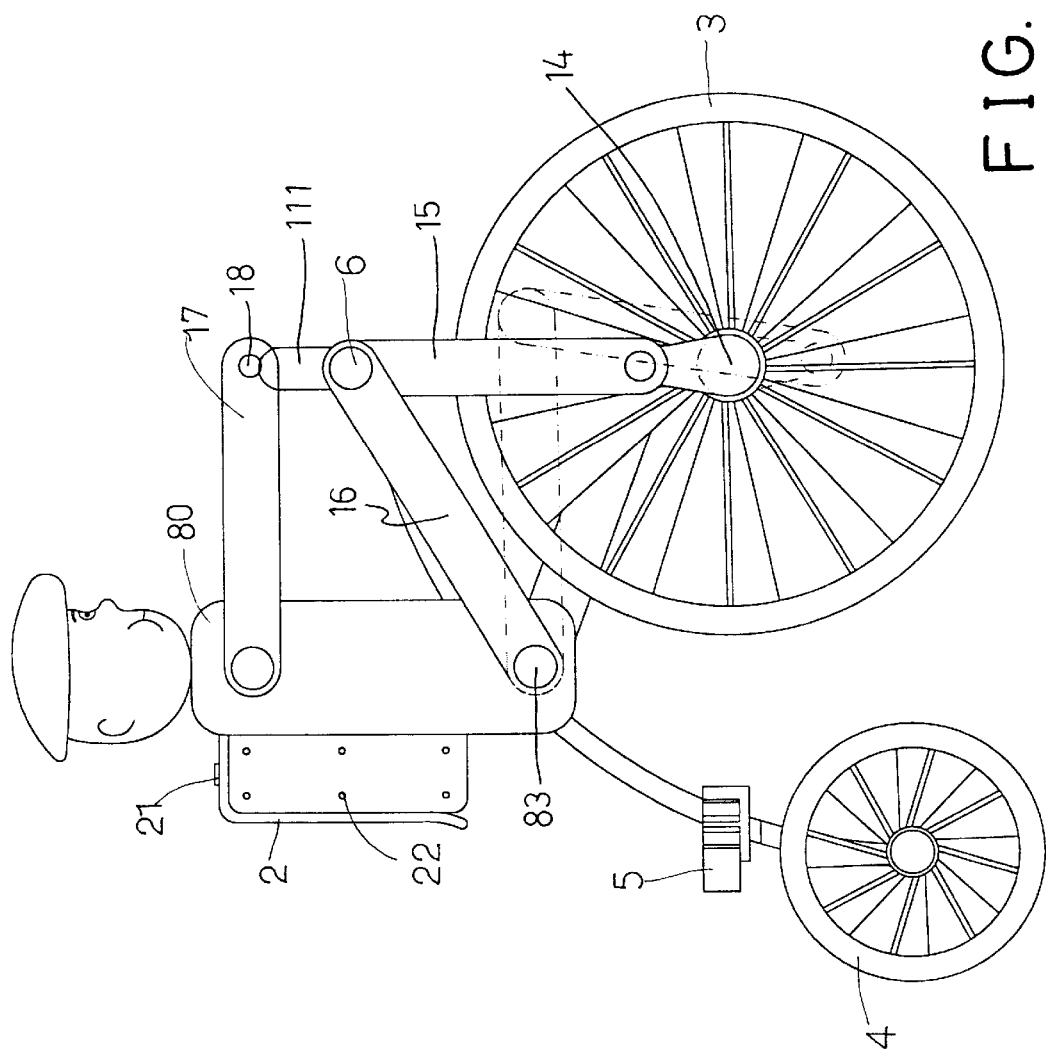

CONTAINER FOR AROMATIC MATERIALS

BACKGROUND OF THE INVENTION

1. Field of the Invention

The present invention relates to a container, and more particularly to a container for aromatic materials.

2. Description of the Prior Art

Typical containers for aromatic materials comprise a predetermined configuration having a chamber formed therein for receiving the aromatic materials. When the aromatic materials have been consumed, any other aromatic materials may not be added or inserted into the container.

The present invention has arisen to mitigate and/or obviate the afore-described disadvantages of the conventional containers for aromatic materials.

SUMMARY OF THE INVENTION

The primary objective of the present invention is to provide a container for receiving the aromatic materials and for allowing the aromatic materials to be added and inserted into the container.

The other objective of the present invention is to provide a container for receiving the aromatic materials which includes one or more rotatable wheels and/or which includes a light device for generating lights.

In accordance with one aspect of the invention, there is provided a container for an aromatic material, the container comprising a block, a housing attached to the block for receiving the aromatic material, the housing including an opening formed therein for inserting the aromatic material into the housing, and including a plurality of orifices formed therein for allowing air to blow a perfume of the aromatic material out of the housing, at least one leg including a first end pivotally coupled to the block at a pivot pole, and means for rotating the leg about the pivot pole.

A frame is further provided for supporting the block, at least one wheel is rotatably attached to the frame, and means for coupling the wheel to the leg and to drive the leg to rotate about the pivot pole. The coupling means includes at least one crank secured to the wheel, and a link pivotally couples the crank to the leg for driving the leg to rotate about the pivot pole when the wheel is rotated. The frame includes a track provided therein, the block is slidably supported on the track of the frame. The block includes a channel formed therein for receiving the track of the frame and allowing the block to be slided along the track of the frame. The frame includes a pivot shaft, the block further includes at least one arm having a first end pivotally coupled to the block and having a second end pivotally coupled to the frame at the pivot shaft.

An attaching device is further provided for attaching the block to a supporting object. A light bulb is further attached to the block, and a switch is coupled to the light bulb, the link includes an extension extended therefrom for actuating the switch when the link is moved by the wheel.

Further objectives and advantages of the present invention will become apparent from a careful reading of a detailed description provided hereinbelow, with appropriate reference to accompanying drawings.

BRIEF DESCRIPTION OF THE DRAWINGS

FIGS. 3, 4, 5 are side views illustrating the applications of the container.

DETAILED DESCRIPTION OF THE PREFERRED EMBODIMENT

Figure 1:
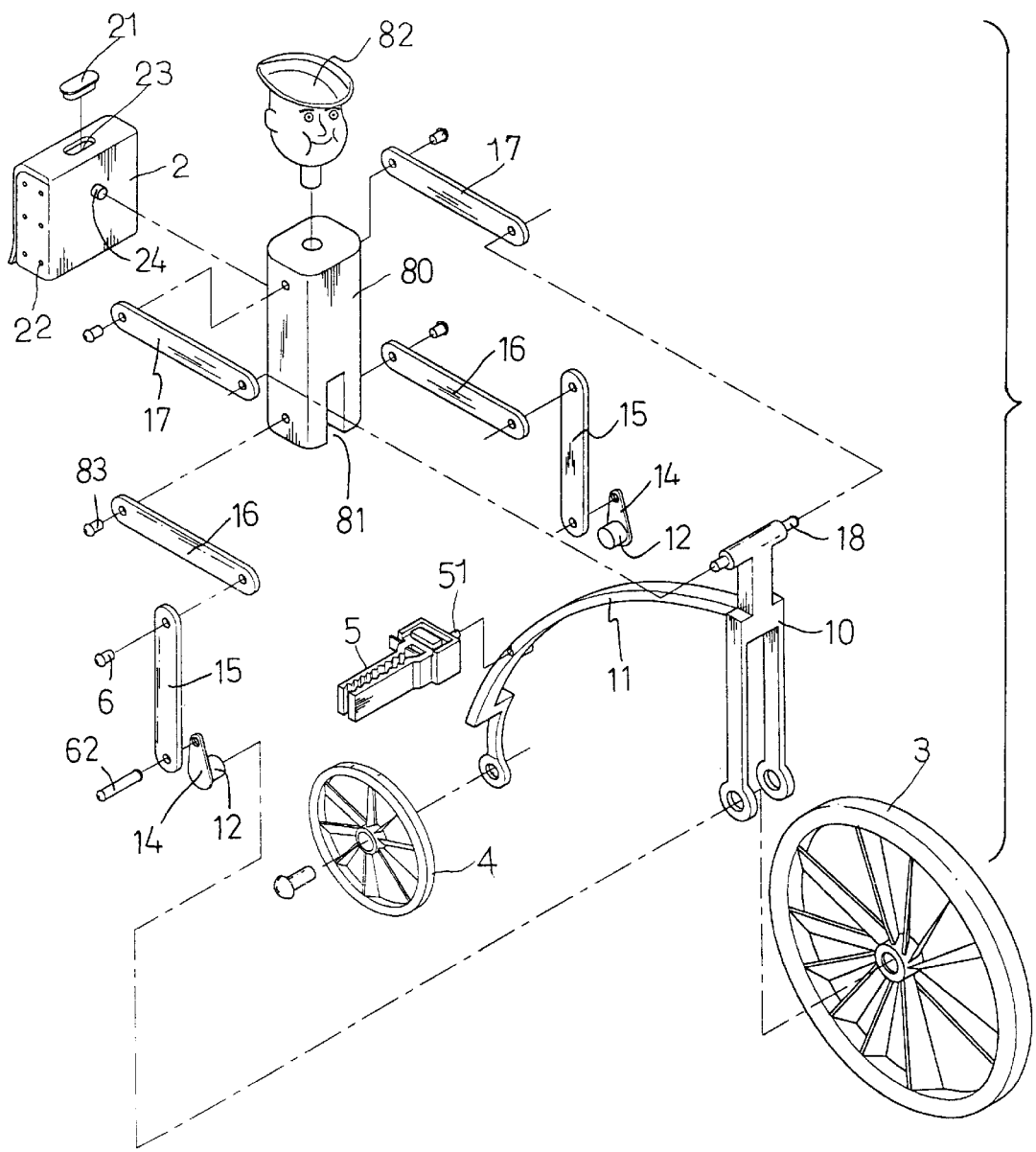
FIG. 1 is an exploded view of a container for aromatic materials in accordance with the present invention.
Figure 2:
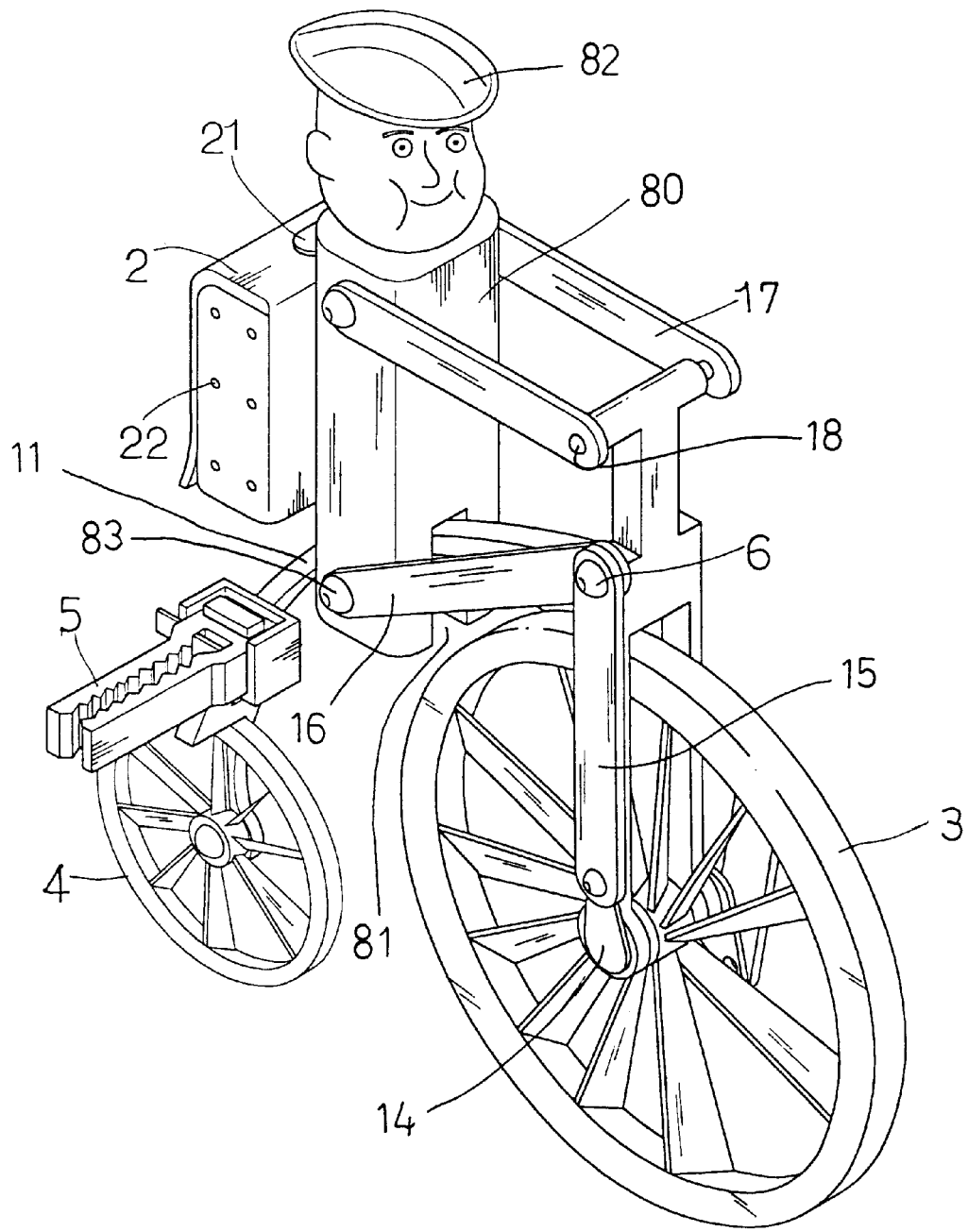
FIG. 2 is a perspective view of the container.
Figure 5:
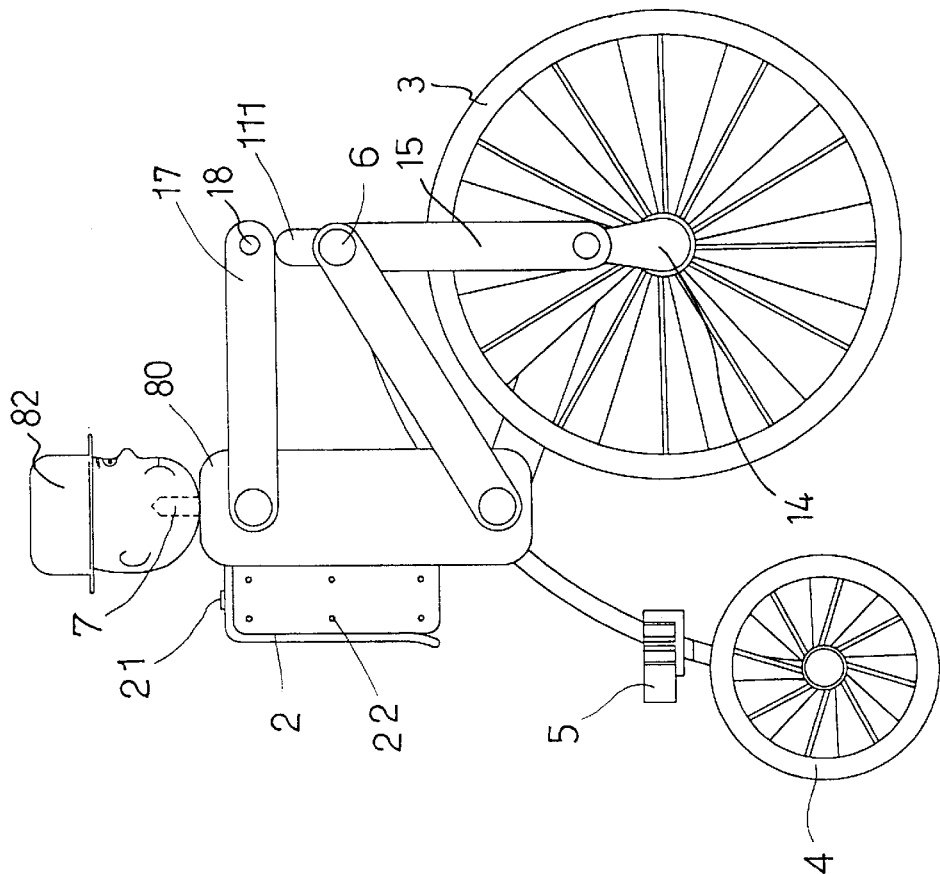
Figure 4:
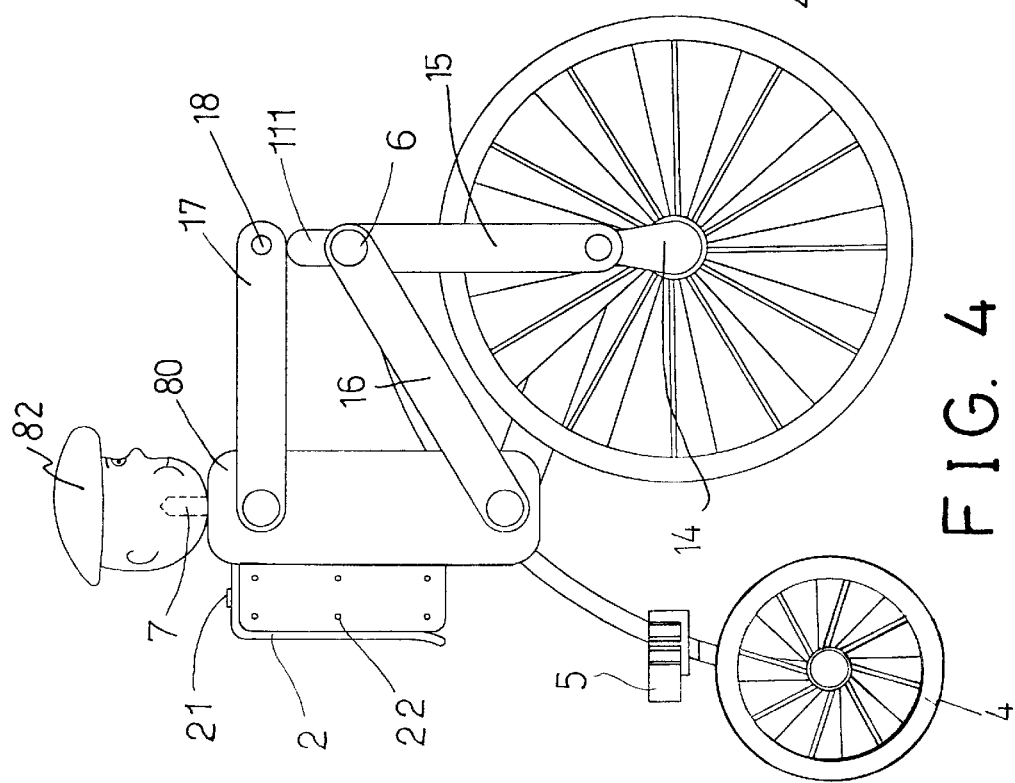
Figure 6:
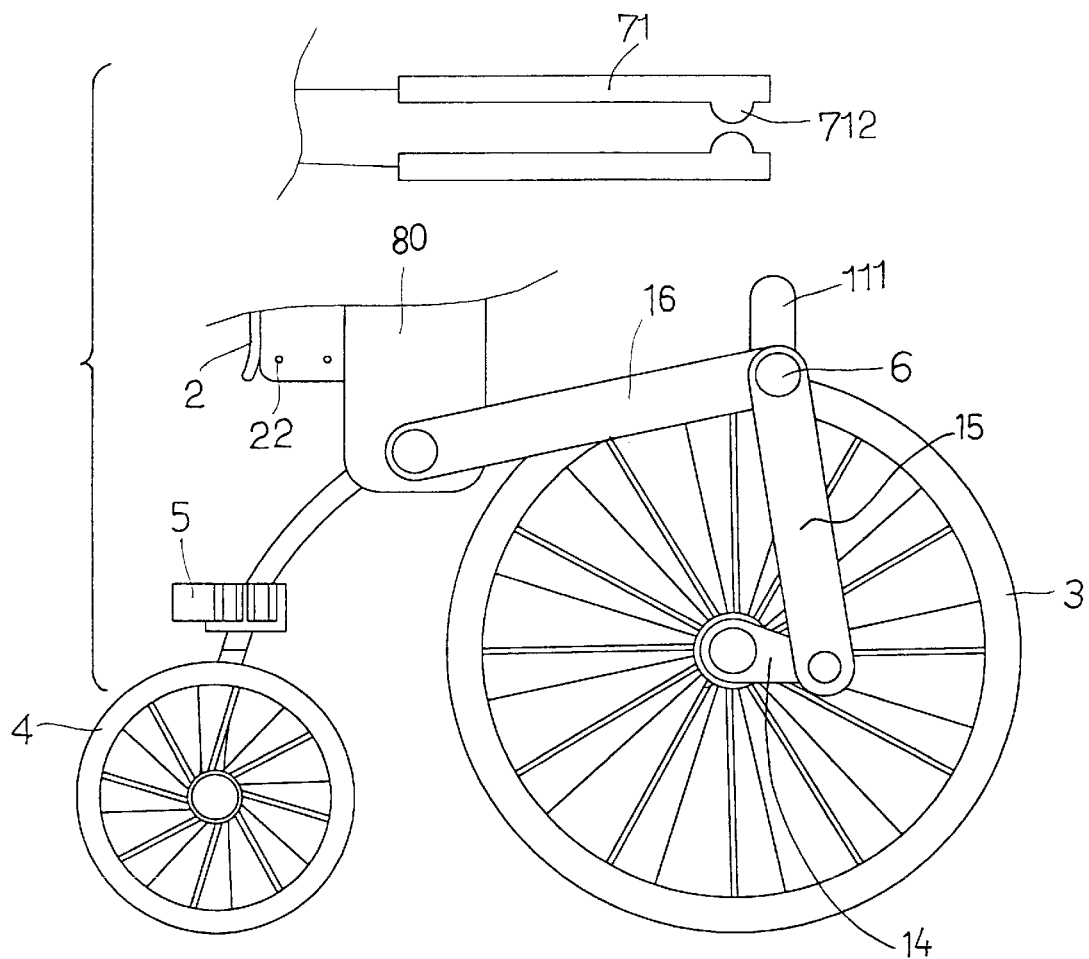
FIGS. 6 and 7 are partial side views illustrating the operation of the container.
Figure 7:
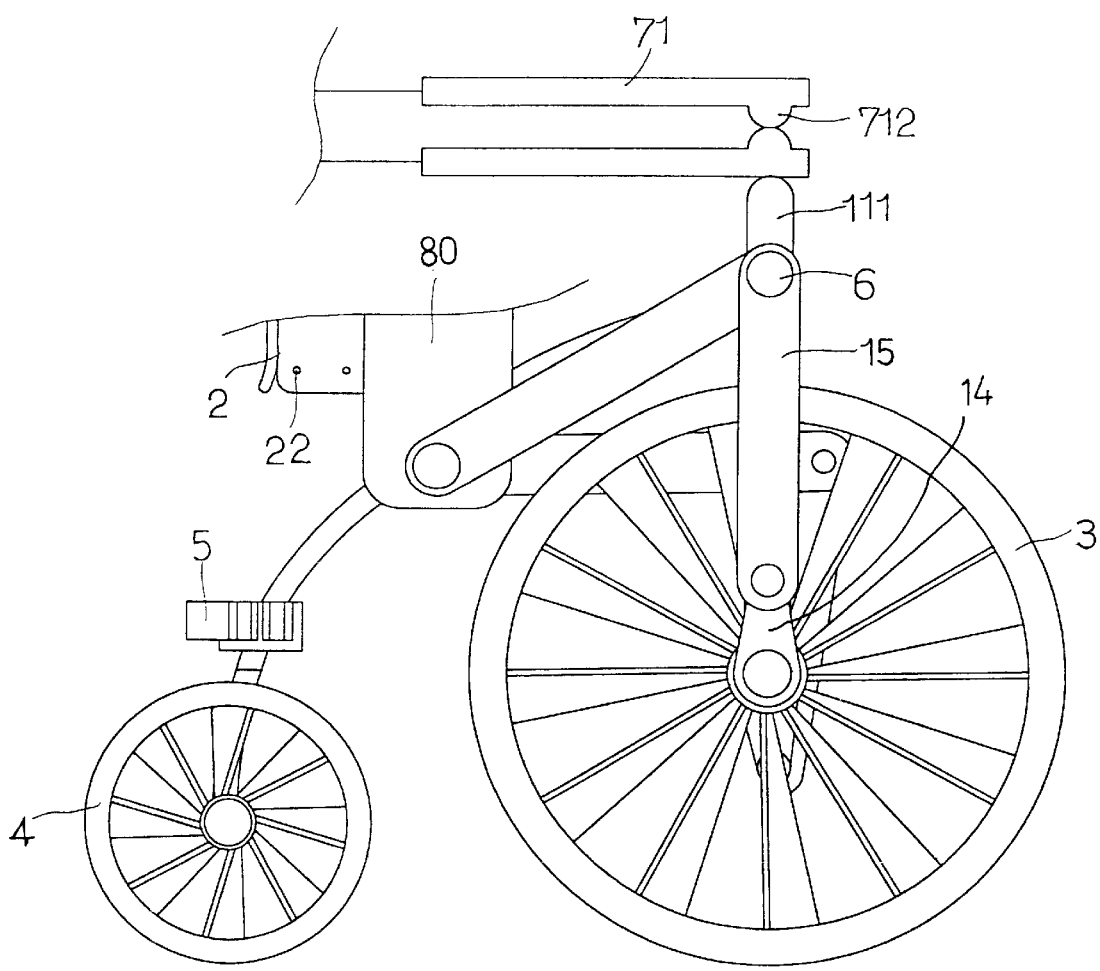

Referring to the drawings, and initially to FIGS. 1–3, a container in accordance with the present invention is particularly provided for containing the aromatic materials and comprises a frame 10 including a curved track 11 provided therein and including a wheel 3 rotatably secured to the front portion thereof at one or more pivot pins 12 and another wheel 4 rotatably secured to the rear portion thereof. The pivot pins 12 are secured to the wheel 3 and rotated in concert with the wheel 3. Two cranks 14 each has one end secured to or extended from the respective pivot pins 12 and rotated in concert with the pivot pins 12. A block 80 includes a channel 81 formed in the bottom for slidably receiving the track 11 of the frame 10 and for allowing the block 80 to be moved along the track 11. A head 82 is detachably secured on top of the block 80 and may include various kinds of shapes (FIGS. 4, 5). A pair of arms 17 pivotally couple the upper portion of the block 80 to the pivot shaft 18 of the frame 10. One or more legs 16 each has a rear end pivotally coupled to the lower portion of the block 80 at a pivot pole 83 and each has a front end pivotally coupled to a pair of links 15 respectively at a pivot axle 16. The links 15 are pivotally coupled to the cranks 12 at a pivot rod 62 respectively.

A housing 2 includes a projection 24 engaged into the block 80 and secured to the block 80 by such as a force-fitted engagement, or by adhesive materials, or by the other fasteners. The housing 2 includes a chamber formed therein for receiving the aromatic materials, which are preferably in solid state, and includes an opening 23 formed in the upper portion for adding or for inserting the aromatic materials into the housing 2. A cap 21 may be attached to the housing 2 for enclosing the opening 23 of the housing 2. The housing 2 includes a number of orifices 22 formed therein, particularly formed in the side portions thereof for allowing the air to flow into the housing 2 and to blow the perfume of the aromatic materials out of the housing 2. A securing device, such as a clipper 5, includes a projection 51 engaged into the frame 10 for securing the aromatic material container to any supporting object, particularly for securing the container to the air exit of the air conditioner of the vehicle. Alternatively, without the clipper 5, the container may also be hung onto a support object by the frame 10 or by the other hook devices.

In operation, as shown in FIGS. 3 and 4, when the container is attached to the air exit of the air conditioner of the vehicle, the air from the air conditioner of the vehicle may flow through the orifices 22 of the housing 2 to blow the perfume of the aromatic materials out of the housing 2. In addition, when the air flows through the wheel 3, the wheel 3 may be driven by the air, and the block 80 may thus be caused to move along the track 11 of the frame 10 by the cranks 14, the links 15 and the legs 16, such that the elements may simulate the bicycle riding. The legs 16 may be caused to rotate about the pivot pole 83. The arms 17 may also be caused to slightly rotate about the pivot shaft 18.

Referring next to FIGS. 4 and 5, a light bulb 7 may further be disposed in the block 80, particularly in the head 82 of the block 80. One of the links 15 includes an extension 111 extended therefrom (FIGS. 3–7). A switch 71 (FIGS. 6, 7) is coupled to the light bulb 7 and includes a pair of contacts 712 to be actuated by the extension 111 of the link 15. The contacts 712 may be forced to be contacted with each other (FIG. 7) when the extension 111 of the link 15 is moved upward by the wheel 3 via the crank 14 in order to energize the light bulb 7 to generate a flash light.

Accordingly, the container in accordance with the present invention may be used for receiving the aromatic materials and for allowing the aromatic materials to be added and inserted into the container, and may include one or more rotatable wheels and/or a light device for generating lights.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

I claim:

1. A container for an aromatic material, said container comprising:

a block, a housing attached to said block for receiving the aromatic material, said housing including an opening formed therein for inserting the aromatic material into said housing, and including a plurality of orifices formed therein for allowing air to blow a perfume of the aromatic material out of said housing, at least one leg including a first end pivotally coupled to said block at a pivot pole, and means for rotating said at least one leg about said pivot pole.

2. The container according to claim 1 further comprising a frame for supporting said block, at least one wheel rotatably attached to said frame, and means for coupling said at least one wheel to said at least one leg and to drive said at least one leg to rotate about said pivot pole.

3. The container according to claim 2, wherein said coupling means includes at least one crank secured to said at least one wheel, and a link pivotally couples said at least one crank to said at least one leg for driving said at least one leg to rotate about said pivot pole when said at least one wheel is rotated.

4. The container according to claim 2, wherein said frame includes a track provided therein, said block is slidably supported on said track of said frame.

5. The container according to claim 4, wherein said block includes a channel formed therein for receiving said track of said frame and allowing said block to be slided along said track of said frame.

6. The container according to claim 2, wherein said frame includes a pivot shaft, said block further includes at least one arm having a first end pivotally coupled to said block and having a second end pivotally coupled to said frame at said pivot shaft.

7. The container according to claim 1 further comprising means for attaching said block to a supporting object.

8. The container according to claim 1 further comprising means for generating a light.

9. The container according to claim 1 further comprising a light bulb attached to said block, and means for energizing said light bulb.

10. The container according to claim 3 further comprising a light bulb attached to said block, a switch coupled to said light bulb, said link including an extension extended therefrom for actuating said switch when said link is moved by said at least one wheel.

11. A container for an aromatic material, said container comprising:

a frame including a track provided therein, a block slidably supported on said track of said frame, a housing attached to said block for receiving the aromatic material, said housing including a plurality of orifices formed therein for allowing a perfume of the aromatic material to be blown out of said housing, and means for moving said block along said track of said frame.

* * * * *